United States Patent
Gottuso

(12) 
(10) Patent No.: US 6,524,528 B1
(45) Date of Patent: Feb. 25, 2003

(54) METHOD OF STERILIZING A TATTOOING SOLUTION THROUGH IRRADIATION

(76) Inventor: Suzanne C. Gottuso, 95 Buttonwood Dr., Fair Haven, NJ (US) 07704

(*) Notice: Subject to any disclaimer, the term of this patent is extended or adjusted under 35 U.S.C. 154(b) by 0 days.

(21) Appl. No.: 09/260,122

(22) Filed: Mar. 2, 1999

(51) Int. Cl.[7] ................................. A61L 2/08
(52) U.S. Cl. ........................................ 422/22
(58) Field of Search ....................... 422/22; 106/31.64, 106/31.85, 472; 424/10.1, 63, 125

(56) References Cited

U.S. PATENT DOCUMENTS

| | | | | |
|---|---|---|---|---|
| 3,779,706 A | * | 12/1973 | Nablo | 422/22 |
| 5,362,442 A | * | 11/1994 | Kent | 422/22 |
| 5,609,866 A | | 3/1997 | Khan et al. | 424/78.25 |
| 5,712,894 A | | 1/1998 | Lanotte | 378/68 |
| 5,730,933 A | | 3/1998 | Peterson | 422/22 |
| 5,948,123 A | * | 9/1999 | Hirata et al. | 8/404 |

OTHER PUBLICATIONS

Shatz, et al. "Inflammatory Bowel Disease After India Ink Tattooing: Too Much of a Good Thing", vol. 51, No. 2, Gastrointestinal Endoscopy, p. 253, 2000.

Hammond "Sterility of India Ink", vol. 40, Gastrointestinal Endoscopy, pp. 519–520, 1994.

B.A. Shatz, L.B. Weinstock, P.E. Swanson, E.P. Thyssen "Long–Term Safety of India Ink Tattoos in the Colon", Gastrointestinal Endoscopy, vol. 45, No. 2, 1997.

R. Nizam, N. Siddiqi, S.K. Landas, D.S. Kaplan, P.G. Holtzapple "Colonic Tattooing with India Ink: Benefits, Risks, and Alternatives", American Journal of Gastroenterology, vol. 91, No. 9, 1996.

P.Salomon, J.S. Berner, J.D. Wayne "Endoscopic India Ink Injection: a Method for Preparation, Sterilization, and Administration", Gastrointestinal Endoscopy, vol. 39, No. 6, 1993.

"Endoscopic Tissue Staining And Tattooing" American Society for Gastrointestinal Endoscopy, Oct. 1995.

\* cited by examiner

*Primary Examiner*—Elizabeth McKane
(74) *Attorney, Agent, or Firm*—Moser, Patterson & Sheridan LLP

(57) ABSTRACT

A method of sterilizing a tattooing solution through irradiation. Specifically, a tattooing solution such as an india ink solution is supplied and irradiated to facilitate sterilization. The radiation is, for example, gamma radiation.

16 Claims, 1 Drawing Sheet

METHOD OF STERILIZING A TATTOOING SOLUTION THROUGH IRRADIATION

BACKGROUND OF THE DISCLOSURE

1. Field of the Invention

The invention relates generally to a method for sterilizing liquids and, more particularly, the invention relates to a method for sterilizing a tattooing solution through irradiation.

2. Description of the Background Art

Endoscopists have used tattoos to permanently mark specific sites in the colon that require follow-up examination. Such marking enables the endoscopist to easily find the marked location and perform the follow-up exam. Since tattooing with a substance such as india ink is permanent, such marking allows follow-up examinations to be performed over a long period of time. As such, the injected india ink may remain in the colonic tissue for 20 to 30 years. Alternatively, a tattoo may be used for short term, preoperative marking wherein an endoscopist can identify and mark regions of concern in the colon and, during an operation, the marked region of the colon can be easily identified by the surgeon. In both cases, concerns were raised about the safety of the use of india ink as a colonic marker. There were reports that the use of unsterilized or improperly sterilized india ink caused influenza, infection, phlegmonous gastritis, fat necrosis with inflammatory pseudotumor and abscesses.

To combat the problems associated with the use of india ink for colonic tattooing, physicians have begun requiring the ink be sterilized prior to use. One sterilization process that has been used combines india ink with bacteriostatic sterile water, then filters the solution with a 5 $\mu$m Travenol particulate filter, and lastly autoclaves the solution in 10 ml aliquots at 250° F. for 40 minutes. This process is messy, time consuming and the use of the 5 $\mu$m filter can remove a substantial amount of carbon black from the solution. Additionally, there is no standardized filtration process for sterilizing india ink. Consequently, the degree of sterilization varies from batch to batch.

Therefore, a need exists in the art for a method of sterilizing tattooing solutions that is simple, less time consuming, and repeatable from batch to batch.

SUMMARY OF THE INVENTION

The disadvantages heretofore associated with the prior art are overcome by a method of sterilizing tattooing solutions (e.g., india ink) through irradiation. In an illustrative embodiment of the invention, india ink is mixed in a saline solution, the mixture is covered with a paraffin film and sonicated, the mixture is then filtered through a 20 micron filter, then packaged and sealed. The packaged product is exposed to gamma radiation sufficient to sterilize the india ink solution.

BRIEF DESCRIPTION OF THE DRAWING

The teachings of the present invention can be readily understood by considering the following detailed description in conjunction with the accompanying drawing in which.

DETAILED DESCRIPTION

Figure 1:
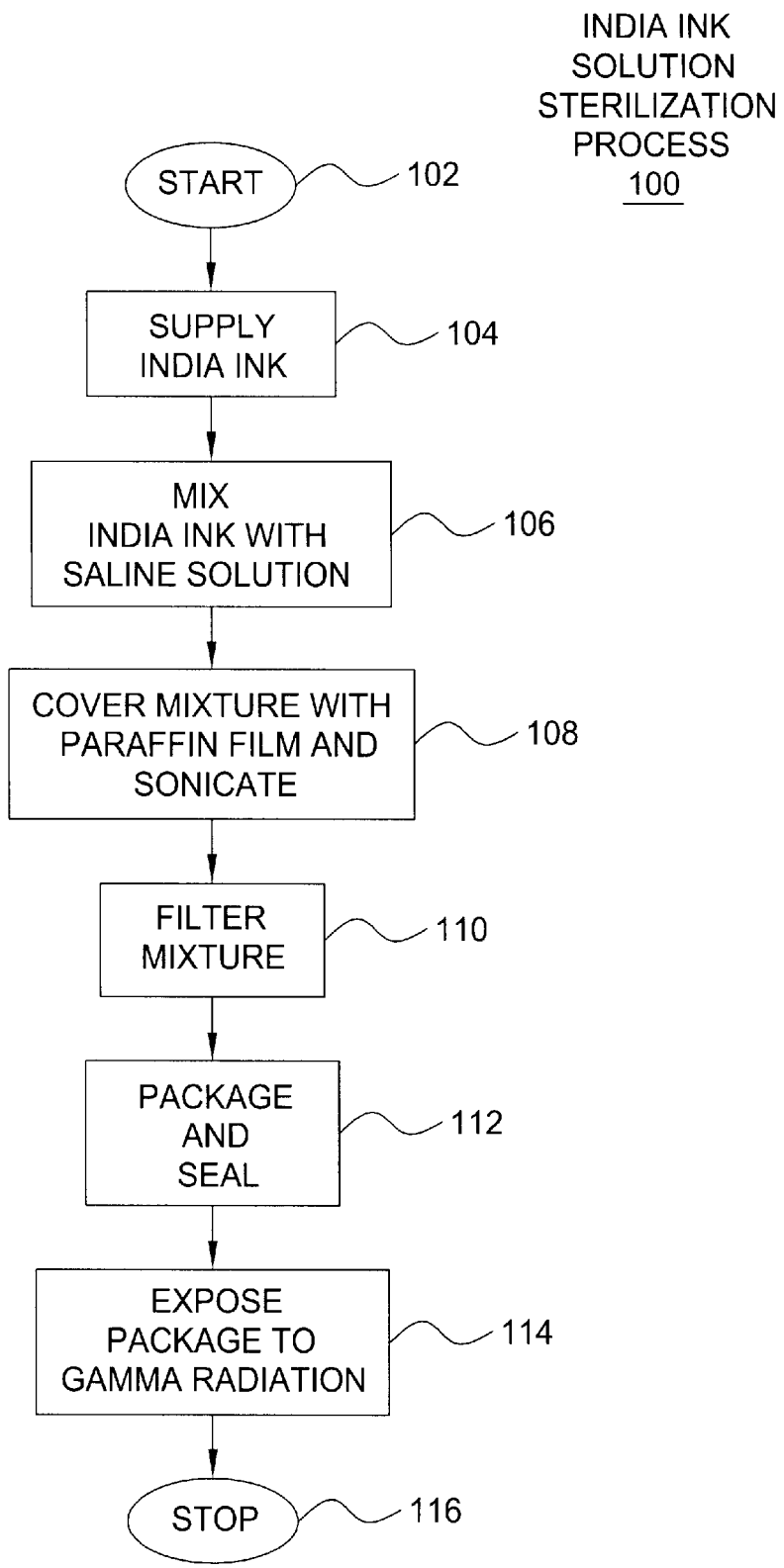
FIG. 1 depicts a flow diagram of the method of the present invention.

FIG. 1 depicts a flow diagram that represents the process of the present invention for sterilizing a tattooing solution through irradiation. The process 100 starts at step 102 and proceeds to step 104 wherein a tattooing material such as india ink is supplied. India ink generally comprises carbon black in an aqueous or alcohol solution with various stabilizers. At step 106, the india ink is mixed with a saline solution to form an ink mixture. The ratio of ink to saline is generally in the range of 1:10 to 1:100, with a preferred mixture of 1:50. In step 108, the ink mixture is placed in a beaker, covered with a paraffin film and sonicated for one-half hour. At step 110, the sonicated mixture is then filtered through a 20 micron filter to remove any agglomerates of carbon black. At step 112, the filtered mixture is packaged and sealed in a plurality of tamper resistant glass containers. Each glass container or vial generally contains 0.375 fluid ounces of the mixture. Of course, other size vials may be used.

The glass vials containing the mixture are, at step 114, irradiated. In this embodiment of the invention, the radiation used is gamma radiation. The gamma radiation is applied for anywhere from 225–500 minutes with a dose in the range of 20–40 kGy. Such exposure sterilizes the ink mixture such that the problems that arise from using unsterilized or improperly sterilized ink mixtures are overcome. The process stops at step 116.

Although the foregoing embodiment of the invention sterilizes india ink, the technique of the present invention can be used to sterilize other tattooing solutions such as iron oxide. In an alternative embodiment, iron oxide is diluted with glycerol and alcohol, sonicated, filtered, packaged and then irradiated to sterilize the solution. It is believed that any tattooing ink or dye will be advantageously affected by sterilization performed in accordance with the present invention.

Another alternative embodiment of the invention uses other forms of radiation in lieu of gamma radiation. For example, an electron beam may be used to sterilize a tattooing solution in accordance with the invention.

Although various embodiments which incorporate the teachings of the present invention have been shown and described in detail herein, those skilled in the art can readily devise many other varied embodiments that still incorporate these teachings.

What is claimed is:

1. A method of sterilizing a tattooing solution comprising the steps of:

supplying a tattooing material;

mixing the tattooing material with a second material to form a solution;

sonicating the solution;

filtering the solution using a 20 micron filter; and exposing the solution to radiation at a dosage and for a duration that sterilizes the tattooing solution.

2. The method of claim 1 wherein the radiation is gamma radiation.

3. The method of claim 2 wherein the gamma radiation exposure is 20–40 kGy.

4. The method of claim 3 wherein the duration of exposure is anywhere from 225 to 500 minutes.

5. The method of claim 1 wherein the radiation is an electron beam.

6. The method of claim 1 wherein the sonicating step includes covering the mixture with a paraffin film.

7. A method of sterilizing an india ink solution comprising the steps of:

supplying india ink;

mixing the india ink with a saline solution to form a diluted ink mixture;

covering the ink mixture with a paraffin film and sonicating the mixture;

filtering the mixture using a 20 micron filter;

packaging the mixture into vials; and exposing the vials containing the mixture to gamma radiation.

8. The method of claim 7 wherein the mixing step forms a mixture using between 1:10 to 1:100 ratio of india ink to saline.

9. The method of claim 7 wherein the mixing step forms a mixture using a 1:50 ratio of india ink to saline.

10. The method of claim 7 wherein the gamma radiation exposing step further comprises:

exposing the mixture to a radiation level of 20–40 kGy.

11. The method of claim 10 wherein said exposure occurs for anywhere from 225 to 500 minutes.

12. A method of sterilizing an india ink solution comprising the steps of:

preparing an india ink tattooing solution;

filtering the tattooing solution using a 20 micron filter; and exposing the filtered solution to radiation at a dosage and for a duration that sterilizes the tattooing solution.

13. The method of claim 12, wherein the preparing step further comprises:

mixing the india ink with a saline solution to form a diluted ink mixture; and covering the ink mixture with a paraffin film and sonicating the mixture.

14. The method of claim 12, wherein the exposing step further comprises:

exposing the container containing the mixture to gamma or electron beam radiation.

15. The method of claim 12 wherein the radiation is 20–40 kGy of gamma radiation.

16. The method of claim 15 wherein the duration of exposure is anywhere from 225 to 500 minutes.

* * * * *